United States Patent
Sjaunja (10) Patent No.: US 7,132,660 B2
(45) Date of Patent: Nov. 7, 2006

(54) MID INFRA RED ANALYSIS

(75) Inventor: Lars-Ove Sjaunja, Fibyvägen (SE)

(73) Assignee: Miris AB, Uppsala (SE)

( * ) Notice: Subject to any disclaimer, the term of this patent is extended or adjusted under 35 U.S.C. 154(b) by 265 days.

(21) Appl. No.: 10/471,740

(22) PCT Filed: Mar. 15, 2002

(86) PCT No.: PCT/SE02/00494

§ 371 (c)(1),
(2), (4) Date: Mar. 9, 2004

(87) PCT Pub. No.: WO02/075288

PCT Pub. Date: Sep. 26, 2002

(65) Prior Publication Data

US 2004/0135088 A1 Jul. 15, 2004

(30) Foreign Application Priority Data

Mar. 16, 2001 (SE) ................... 0100931

(51) Int. Cl.
*G01N 21/35* (2006.01)
(52) U.S. Cl. ..................... 250/343
(58) Field of Classification Search ............... 250/343
See application file for complete search history.

(56) References Cited

U.S. PATENT DOCUMENTS

| | | | |
|---|---|---|---|
| 4,247,773 A | 1/1981 | Nexo et al. | |
| 4,447,725 A | 5/1984 | Biggs et al. | |
| 4,663,530 A | 5/1987 | Shields | |
| 5,017,785 A * | 5/1991 | Rasanen | 250/345 |
| 5,343,044 A * | 8/1994 | Sjaunja et al. | 250/339.09 |

FOREIGN PATENT DOCUMENTS

| | | | |
|---|---|---|---|
| EP | 0 382 908 A2 | | 8/1990 |
| FR | 2050525 | * | 4/1971 |
| WO | 93/06460 A1 | | 4/1993 |
| WO | WO 01/04612 A2 | * | 1/2001 |

* cited by examiner

*Primary Examiner*—Constantine Hannaher
(74) *Attorney, Agent, or Firm*—Young & Thompson (57) ABSTRACT

A method of quantitative measurement of fat in a liquid sample by an infrared attenuated technique is disclosed. The fat is present in the form of an emulsion of particles causing Christiansen's effect, i.e. the combined effect of light-scattering and anomalous dispersion. The method comprises transmitting infrared radiation through the sample, determining the infrared absorption of the sample in at least one measurement waveband exhibiting the Christiansen's effect, and with reference to a reference waveband. The wavebands are selected such that the fat determination is essentially independent of the Christiansen's effect. The wavebands are preferably selected such that the fat absorbance, i.e. the difference between the absorbances of the measurement and the reference wavebands, is equal for samples having the same concentration of fat, irrespective of the mean fat particle size in the samples

8 Claims, 11 Drawing Sheets

MID INFRA RED ANALYSIS

The present invention relates generally to the infra red detection of various components in food and food stuffs, e.g. fat, protein, lactose etc. in liquids, especially in milk. In particular it relates to a method of accurate and reproducible determination of the fat concentration/contents in milk. The method enables such detection without the need to homogenize the samples. Elaborate calibration is also eliminated. It also relates to an improved apparatus for such measurements.

BACKGROUND OF THE INVENTION

It is well known that different constituents can be measured in solutions, particularly in milk, by infrared transmission spectroscopy apparatus. In liquids, where particle sizes are of the same magnitude or larger then about ⅓ of the electromagnetic wavelength, light scattering attenuates the transmission. The milkfat in milk is comprised of fat globules with an average diameter of app. 3–4 µm and with largest globules of about 10 µm. The triglycerides have four major absorbance wavebands in the mid infrared regions between 2.5–10 µm, namely at about 3.5, 5.7, 6.8 and 8.6 µm, which are caused by C—H stretching vibrations, C=O stretching vibrations, C—H bending vibrations and C—H rocking/C—C stretching vibrations, respectively. The two first wavebands are exclusively used for the determination of fat in milk, due to their intense absorbance as well as high accuracy (as compared to standard chemical determination e.g. Rose-Gottlieb) in determining the fat content in milk. However, these two wavebands have shown to be afflicted by anomalous dispersion phenomena, giving a large variation in the refractive index across the wavebands. The combination of light-scattering and anomalous dispersion give an increasing distortion in the shape of the fat absorbance peaks as the fat globules size increases. This effect, the so called Christiansen effect, has lead to that all the presently preferred apparatuses are provided with built-in homogenizers. Also known apparatus for infrared determinations are using double wavelength single cuvette system as mentioned in U.S. Pat. No. 4,247,773. In practice, even apparatus having the ability to use full-spectrum, are using traditional wavebands with at least one reference waveband for determination of the major component in milk (fat, protein, lactose), and the milk to be analyzed is homogenized with a built-in homogenizer prior to the determination. As long as the homogenizer is working properly the accuracy of the fat determinations is very good. The absorbance bands above 6 µm are mainly influenced by light scattering and the effect is decreasing as the wavelength increases. Many attempts have been proposed in order to enable determination without homogenization. In the patent application WO 92/17767 a method by using a waveband of approx. 1160–1190 $cm^{-1}$ (8.64 µm) is proposed as a method for measuring the fat content in e.g. milk. However, at this waveband the fat has a weak absorbance and the accuracy (as compared to standard chemical determination) is not nearly as good as what is obtained with the wavebands below 6 µm, in the region of 3.5 and 5.7 µm, The effect of light-scattering can be minimized by using a reference near the fat peak in the region of 8.6–8.7 µm as the scattering is nearly of the same magnitude in both the sample waveband and the reference waveband region. The main reason for using the proposed waveband as in WO 92/17767, was to minimize the interference from other constituents of the emulsion. The proposed waveband has also been disclosed as a total solid or moisture waveband in another patent application (EP 0 404 207 A2, U.S. Pat. No. 4,825,076), which also indicate that the proposed waveband also have high correlation to dry-matter in the milk. In WO 93/06460 an infrared attenuation measuring system is disclosed, and among other things a fat determination method, which is substantially independent on the degree of homogenization.

The need for efficient built-in homogenizers for the infrared determinations causes problems of maintaining the efficiency of the homogenization. The homogenizers are built up with moving parts and are relatively large in size, and therefore it is difficult to develop small in-line infrared sensors. A recent patent application (WO 01/04612) discloses a method and apparatus for measuring the fat content in unhomogenized milk and the variation of light-scattering is compensated by means of at least two statistical parameters. The proposed method is using a single waveband for each constituent and the measurement is repeated for a number of aliquots of a sample. A method that can perform determinations without any homogenization (reduction in the fat globule size) and still having a high accuracy means considerable simplification and improvements in development of apparatus. The possibility of making small, simple and robust apparatus with high accuracy, implies that cow-side and in-line apparatus can be produced. This is also an urgent need for developing countries since existing apparatus is expensive and/or developed for large-scale laboratories.

SUMMARY OF THE INVENTION

In view of the problem of performing easy on-site analysis of fat in liquid samples, i.a. in milk with respect to e.g. its fat contents, it is the object of the present invention to provide a versatile, easy-to-use method and instrument for the analysis of liquid foodstuffs, in particular milk, on location at a farmers premises.

In particular the method and apparatus according to the invention shall enable such analysis without the need to homogenize the sample prior to analysis.

This object is achieved with the novel method discussed below. Thereby the method comprises quantitative measurement of fat in a liquid sample by an infrared attenuated technique, wherein the fat is present in the form of an emulsion of particles causing Christiansen's effect, i.e. the combined effect of lightscattering and anomalous dispersion. The method comprises transmitting infrared radiation through the sample, determining the infrared absorption of the sample in at least one measurement waveband exhibiting the Christiansen's effect, and with reference to a reference waveband, said wavebands being selected such that the fat determination is essentially independent of the Christiansen's effect.

In a preferred embodiment of the method, said wavebands are selected such that the fat absorbance, i.e. the difference between the absorbances of the measurement and the reference wavebands, is equal for samples having the same concentration of fat, irrespective of the mean fat particle size in said samples.

More preferably, the measurement waveband(s) is(are) selected to give a higher absorbance for fat with a large mean particle size than for fat with a small mean particle size, and the change in absorbance of said reference waveband between different mean particle sizes is positively correlated with the change in absorbance of said measurement wavebands for different mean particle size.

Still more preferred, an average of measurement wavebands is calculated, said measurement wavebands being inversely influenced by the variation of said mean particle size.

In a further aspect the invention provides an inventive filter combination employed, the effect of which is to eliminate the Christiansen effect, the filter device being discussed below. In a further embodiment the inventive filter can also be implemented by software, e.g. by a suitable application of the FFT (Fast Fourier Transform).

In a further aspect of the invention there is also provided a system for on-site analysis.

Thereby, the system according to the invention comprises a pulsed light source and the inventive filter device. The pulsed light source, in the form of a circuit board having the light source integrated therein, is positioned in close proximity to the cuvette, which makes an extremely compact design, in particular if the detector is also of a circuit board type of design, and is positioned in close proximity to the cuvette on the opposite side.

BRIEF DESCRIPTION OF THE DRAWINGS

FIGS. 11a and b is a schematic illustration of two embodiments of an apparatus according to the invention.

DETAILED DESCRIPTION OF THE INVENTION

As discussed above, the inventor has invented a method and developed an apparatus for the determination of components in milk and other fat-containing liquid samples by using an infra-red spectroscopic absorbance/transmission technique. It comprises selecting the measurement and reference wavebands with specified characteristic, which essentially eliminates the effect of light-scattering and variation in refractive index, the so called Christiansen effect. In a further embodiment more than two measurement wavebands can be selected and interrelated.

Figure 1:
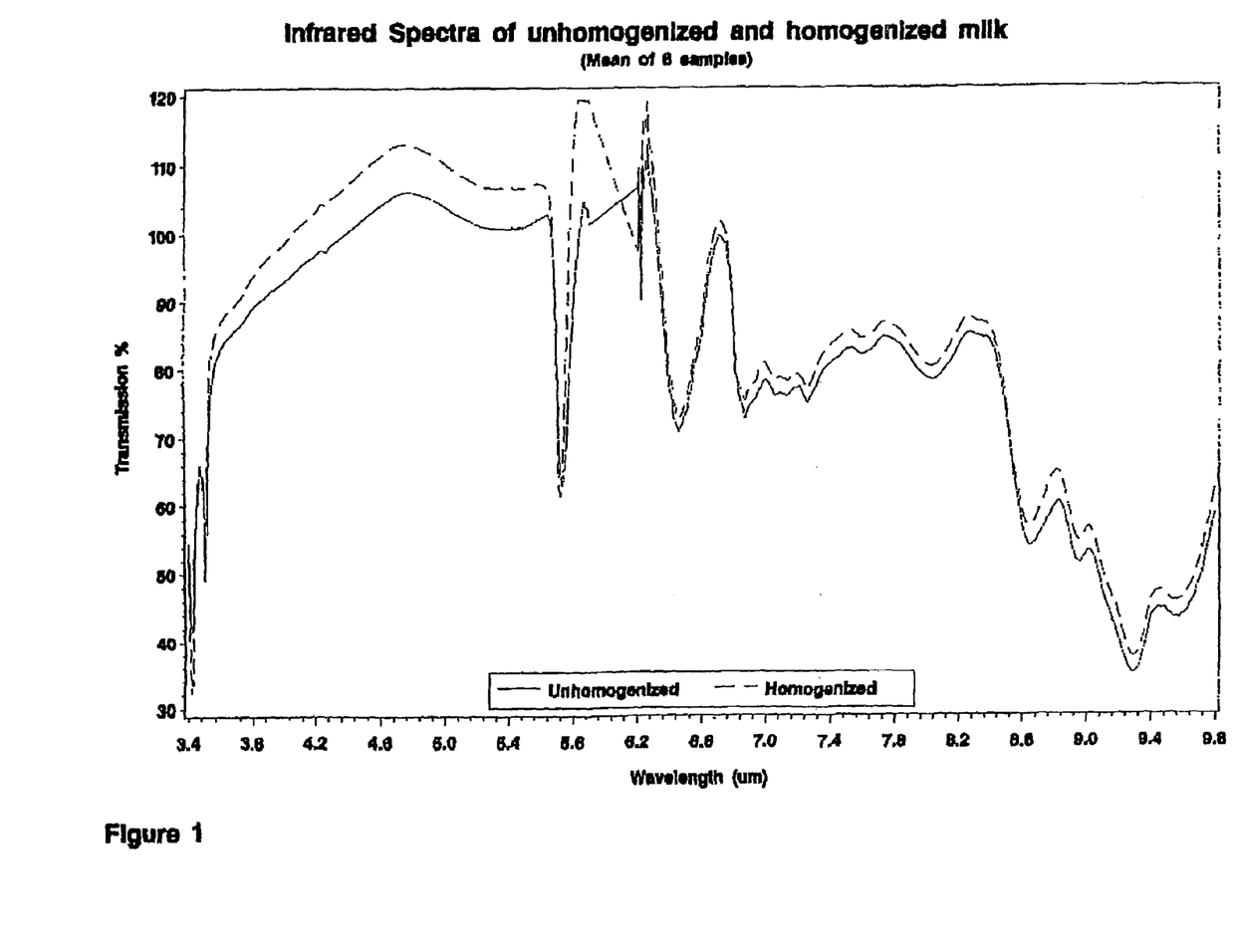
FIG. 1 shows the average difference of transmission spectrum of milk against distilled water of homogenized and unhomogenized samples for the same milk samples.
Figure 2:
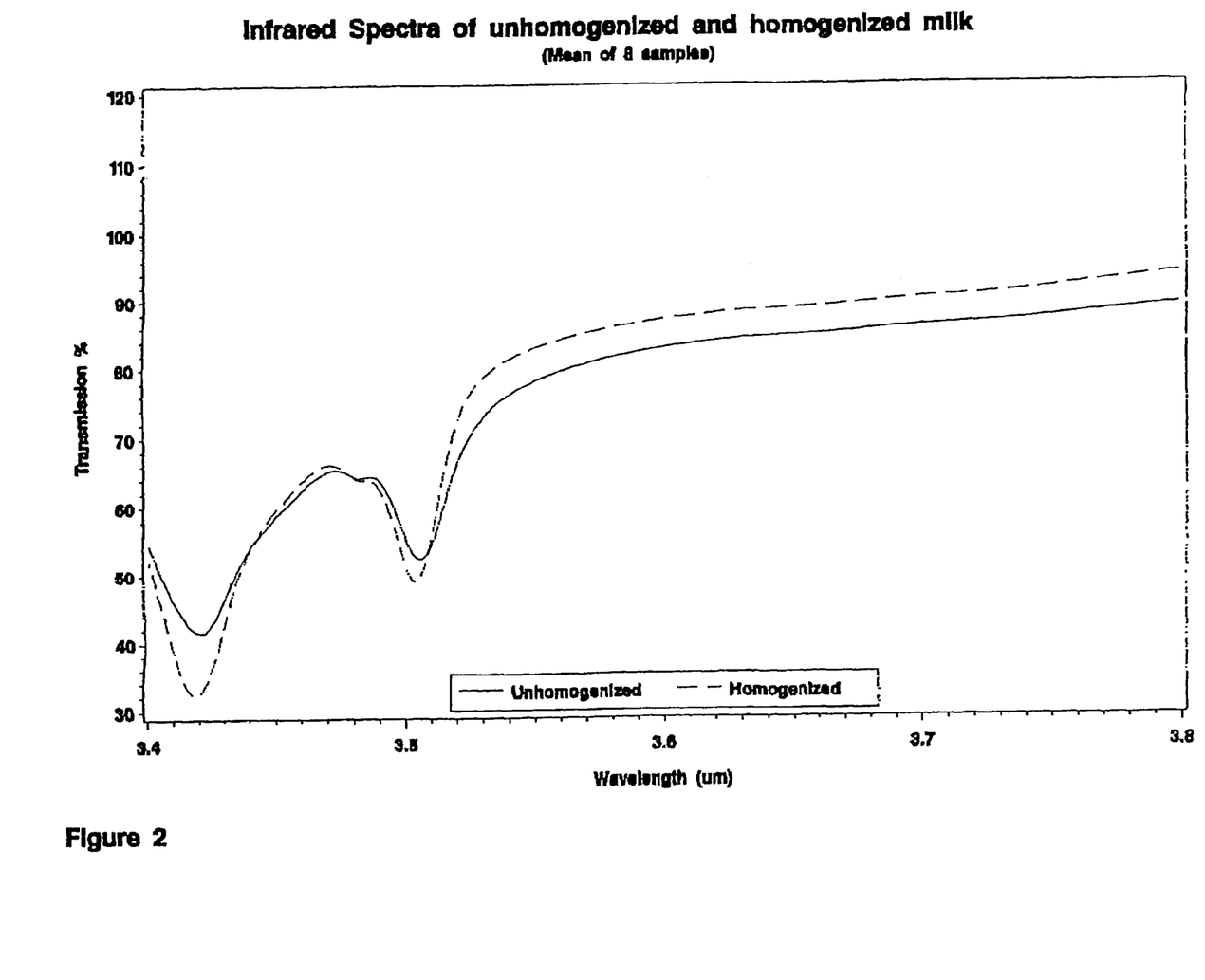
FIG. 2 shows the expanded spectrum of FIG. 1 in the area of C—H stretching vibration region.
Figure 3:
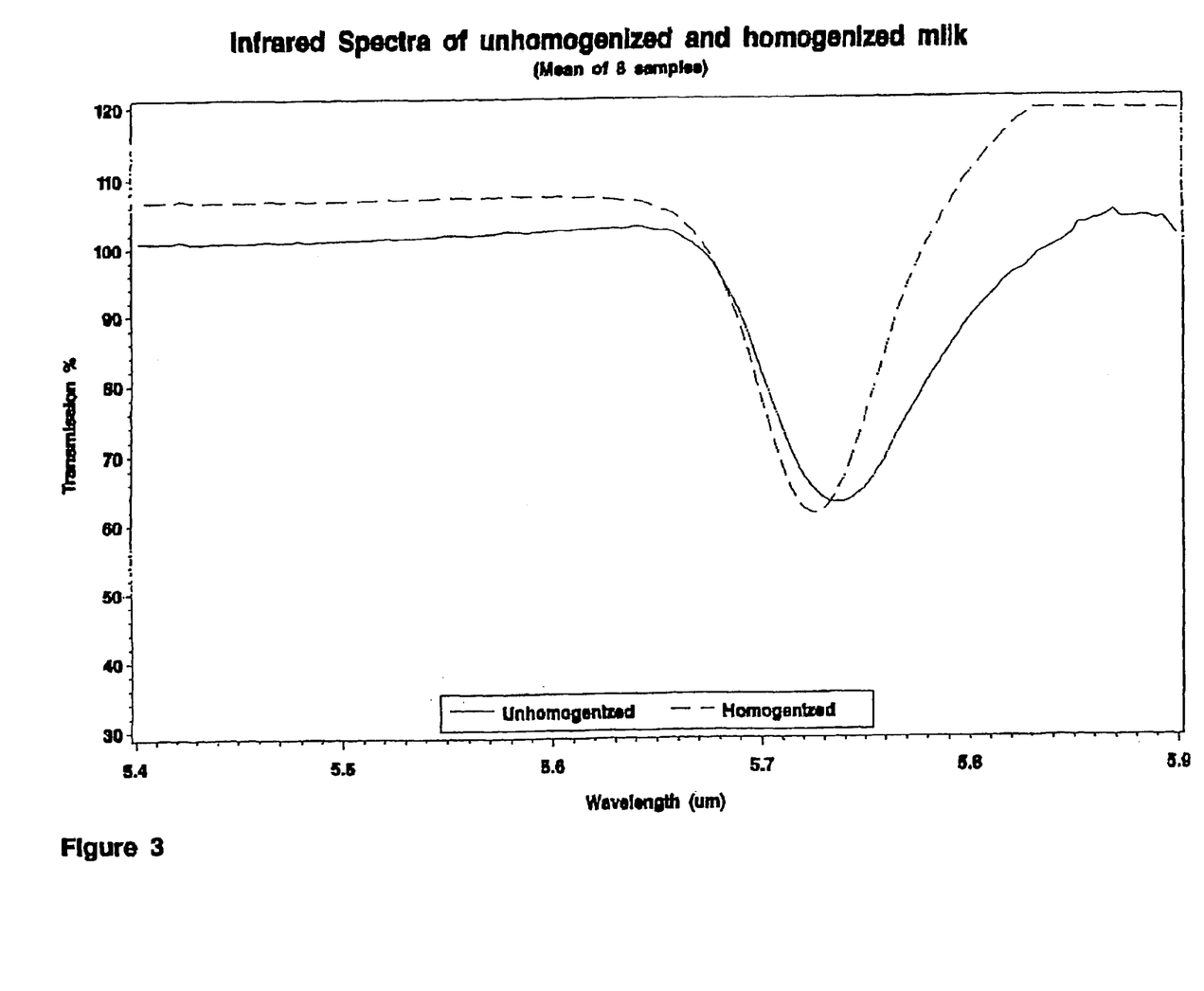
FIG. 3 shows the expanded spectrum of FIG. 1 in the area of C=O stretching vibration region.
Figure 4:
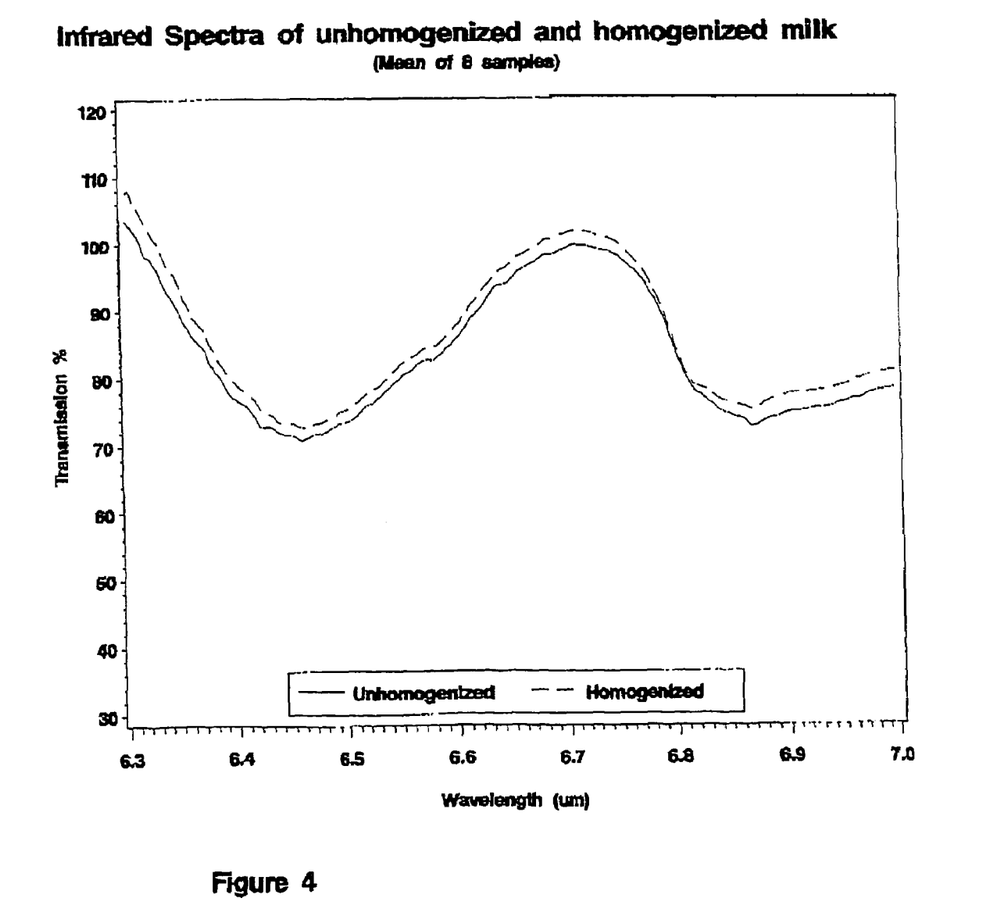
FIG. 4 shows the expanded spectrum of FIG. 1 in the area of C—H bending vibration region.
Figure 5:
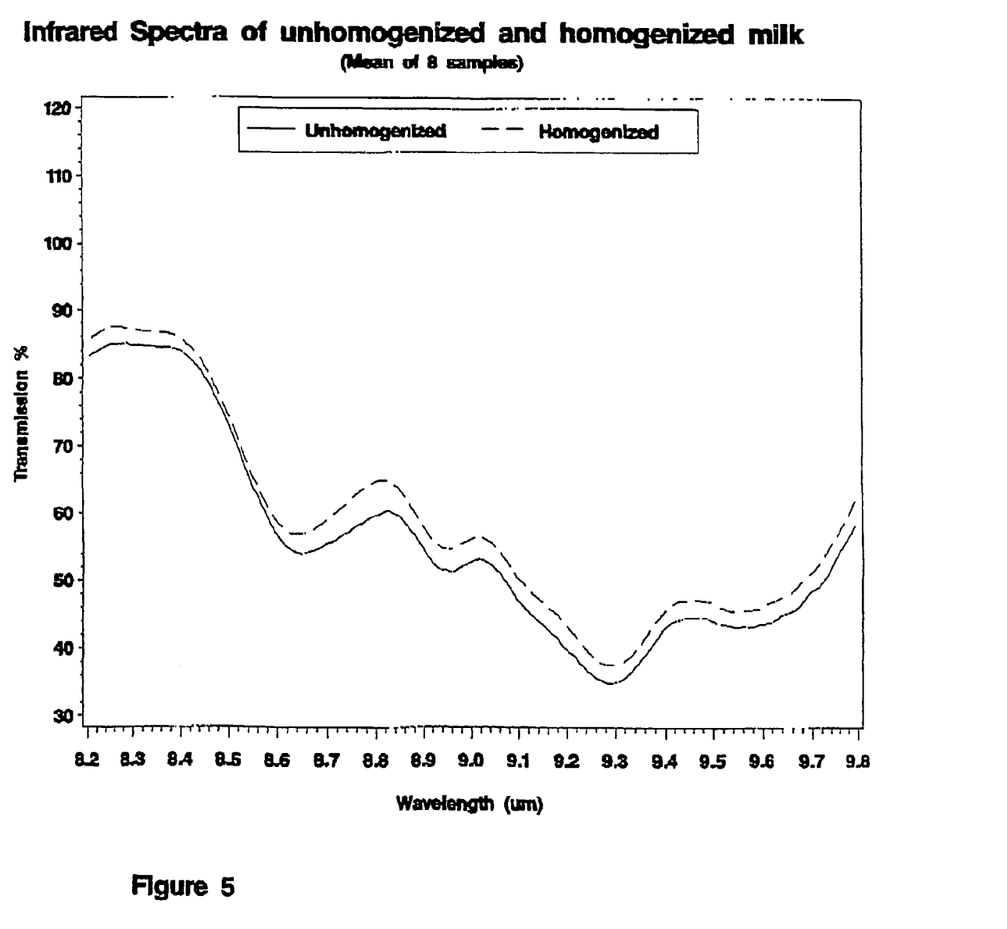
FIG. 5 shows the expanded spectrum of FIG. 1 in the area of C—H rocking/C—C stretching vibration region.

In FIG. 1 the average transmission difference spectrum of unhomogenized and homogenized milk samples is determined with a FTIR spectrometer, Perkin-Elmer 1720. Each of the transmission spectra are given as ratios between distilled water and milk. Eight raw milk samples from individual cows were obtained and each sample divided into 2 subsamples. One set of subsamples was homogenized for 10 sec using a homogenizer, LOSmixer (manufactured by L O SJAUNJA, AB). In FIGS. 2–5 different wavebands regions are expanded. The unhomogenized milk samples have lower transmission as expected, except in the waveband regions of 3.5 μm and 5.7 μm (see FIGS. 2 and 3), which are the absorbance peaks of C—H and C=O stretching vibrations, respectively. The displacement of transmission is decreased as the wavelength is increased. It is well known that large particles in wavebands areas, where refractive index have anomalous dispersion, result in distorted wavebands, giving a displacement of transmission peak towards a longer wavelength, i.e. a less intense band and broadened waveband towards the longer wavelength range. FIGS. 4 and 5 illustrates the regions of the IR spectrum where no crossing-over of the curves occur. In the earlier mentioned method comprising double wavelength and single cuvette, with the reference waveband adjacent (about 0.6 μm above the sample wavebands) to the sample waveband, the Christiansen effect influences the result even more negatively, if the degree of homogenization is changed. In U.S. Pat. No. 4,247,773 it was claimed that there was no significant shift in refractive index in the measuring band around 3.5 μm and therefore a satisfactory compensation was obtained.

From FIGS. 1–3 and from the patent application WO 9306460 it can be concluded that the Christiansen effect exists in regions below 6 μm, where fat is absorbing the infrared energy. The conclusion in '773 of no significant shift in refractive index must obviously be wrong.

The fat globules in uncreamed and raw milk have a mean diameter of about 3 μm with a range about 0.1–10 μm. In the present context the term "uncreamed milk" means milk having no creamed fat layer and the term "raw milk" means milk that is not pasteurized and/or not homogenized. A creamed milk must be carefully and gently mixed, otherwise the fat can be present in the form of aggregates or clumps etc. It is well known that homogenization decreases the mean diameter of the fat globules as well as their distribution. In the present context, the term homogenization means that the natural fat globules are mechanically disrupted into smaller globules, compared to those occurring in a natural state. The term "mixing" means that the flocculated fat globules are converted into their original size. As mentioned before, the light-scattering is a function of the electromagnetic wavelength and the particle size. In the mid infra-red region (2.5–10 μm), used for quantitative determination of milk samples, the fat globules are the major contributors to light-scattering. The other major constituents, like casein micelles, have sizes which are below 0,3 μm and therefore have very little or no light-scattering effect. Known apparatus for infrared determination of milk has a problem of maintaining the efficiency of the built-in homogenizer. For maintaining a good accuracy and precision, the degree of homogenization must have a small variation of the mean fat globule size within and between different milk samples over a time period.

It is known that quantitative infrared determination of milk samples can be performed according to Beer's law, namely that the absorbance is proportional to concentration. In a multi-component solution with interfering components, the concentrations can be determined by linear equations. The linear equations can be estimated by different statistical/mathematical models, namely multiple linear regression (MLR), principal component regression (PCR), partial least-squares (PLS), non linear regression or artificial neural networks (ANN). The chemical results are set up as a function of absorbance values. In situations where at least one or more reference wavebands are used, the absorbance values are the difference between sample and reference wavebands. According to the Beer's law the absorbance of the difference $(A_s-A_r)$ is proportional to concentration according to formula 1:

$$(A_s-A_r)=abc \qquad (1)$$

where a is the absorptivity, b the pathlength and c the concentration. The concentration is predicted according to:

$$c=(A_s-A_r)/ab \qquad (2)$$

In a multicomponent solution, there is more or less some interference from the other components. The interference effect is automatically corrected for by linear equations. This procedure is known and the effects are estimated by the above mentioned statistical methods. By using for example three wavebands, which are highly correlated to fat, protein and lactose, the absorbance difference $(A_s-A_r)$ for each can be substituted by $A_f$, $A_p$ and $A_l$, where f, p and l are denote waveband highly correlated with fat, protein and lactose. The total formula for measuring fat can then be given as:

$$C_f=(1/a_f)A_f-(a_p/a_f)A_p-(a_l/a_f)A_l \qquad (3)$$

This is one way how the measurement is performed in apparatus where compensation is done for interference effects. The number of wavebands can of course be more than three. In apparatus using many wavebands, multivariate statistical methods are used, like PLS, PCR etc.

In situations were the range of concentration is broad, like in for example fat concentration in milk, the absorbance as a function of fat content is non linear. In situations, where the center of the selected waveband is off-set or displaced from the absorbance peak of the measured component, the absorptivity coefficient has a large difference across the waveband. This phenomenon also implies deviation from the linearity relationship between concentration and absorbance. It is well known that calibration equations can be linearized by higher order functions or exponential functions. For example, the interference and linearity parameters can simultaneously be estimated by non linear models according to:

$$C_f=(1/a_f)\log((1-b_2)/(\exp(-A_f)-b_2))-(a_p/a_f)A_p-(a_l-a_f)A_l \qquad (4)$$

By replacing $(1/a_f)$ with $b_1$, $(a_p/a_f)$ with $b_3$ and $(a_l/a_f)$ with $b_4$ the formula can be given as:

$$C_f=b_0+b_1\log((1-b_2)/(\exp(-A_f)-b_2))-b_3A_p-b_4A_l \qquad (5)$$

where:
$C_f$=the concentration of fat
$A_f$=the absorbance value of fat waveband relative to a reference waveband
$A_p$=the absorbance value of protein waveband relative to a reference waveband
$A_l$=the absorbance value of lactose waveband relative to a reference waveband
$b_0$ is a constant
$b_1$, $b_3$, $b_4$ =the coefficients of each waveband
$b_2$=the coefficient of linearity factor of fat waveband It can be observed that the coefficients ($b_1$, $b_3$ and $b_4$) are the absorptivity coefficients as derived from Beer's law.

By suitable selection of at least two wavebands (sample and reference waveband) and selecting a midpoint or center value as well as bandwidth the determination can be independent even if the fat globules have variations in the mean globule size per irradiated volume. This selection is made such that the fat absorbance, i.e. the difference between the absorbances of the measurement and the reference wavebands, is equal for samples having the same concentration of fat, irrespective of the mean fat particle size in said samples. Preferably, said measurement waveband(s) is(are) selected to give a higher absorbance for fat with a large mean particle size than for fat with a small mean particle size, and wherein the change in absorbance of said reference waveband between different mean particle sizes is positively correlated with the change in absorbance of said measurement wavebands for different mean particle size.

Figure 7:
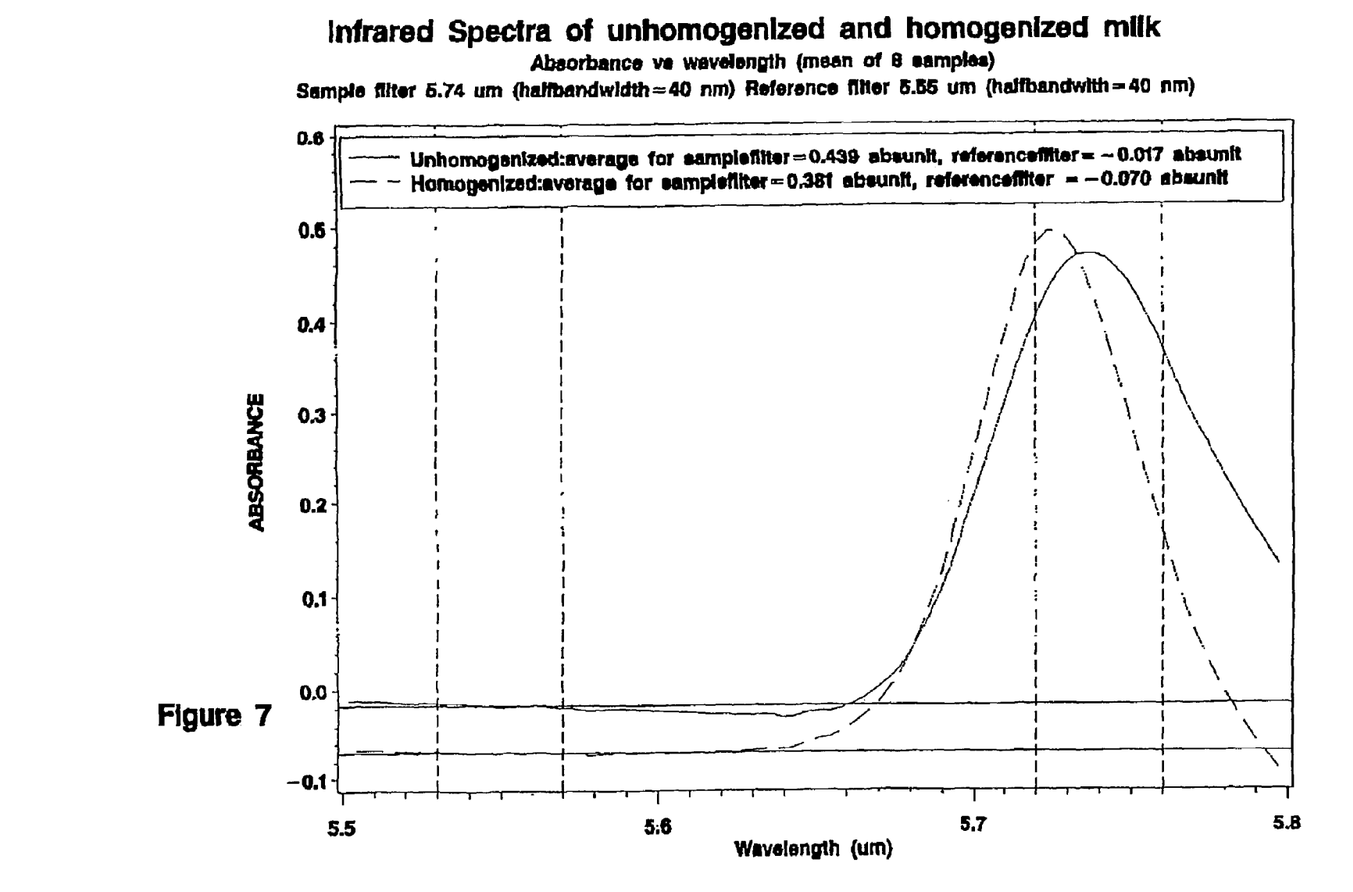
FIG. 7 shows average absorbance spectrum of homogenized and unhomogenized milk samples. The vertical lines are wavebands for reference (center 5.55 μm) and sample (center 5:74 μm) wavebands.

In the present context, the term "waveband" is defined as a wavelength region with a center value and width in which the absorbance or transmission is measured. The center and width of the waveband characteristics are sensitive to temperature and incidence angle of the infrared radiation. The effective waveband characteristics must be validated for the conditions under which they are to be used. The wavebands can be selected by for example narrow band filters (interference filters), gratings, prism, tunable infrared emitters, interferometers etc. In the FTIR (Fourier Transform Infra Red) apparatus, a spectrum is calculated by transforming an interferogram produced by means of an interferometer. The resolution can be found to be less then 1 cm$^{-1}$ and theoretically give bandwidths less than 1 cm$^{-1}$. In FIG. 3 and FIG. 7 it can be seen that by selecting the sample waveband to have an (effective) waveband, which is off-set or displaced from the absorbance peak, the absorbance of unhomogenized milk is higher compared to the absorbance of homogenized milk. This overestimation is counterbalanced by selecting a reference waveband where unhomogenized milks have higher absorbance than homogenized milks.

The compensation of the changed peak shape, due to variations in fat globule size, will be illustrated in the examples given below.

EXAMPLE 1

Figure 6:
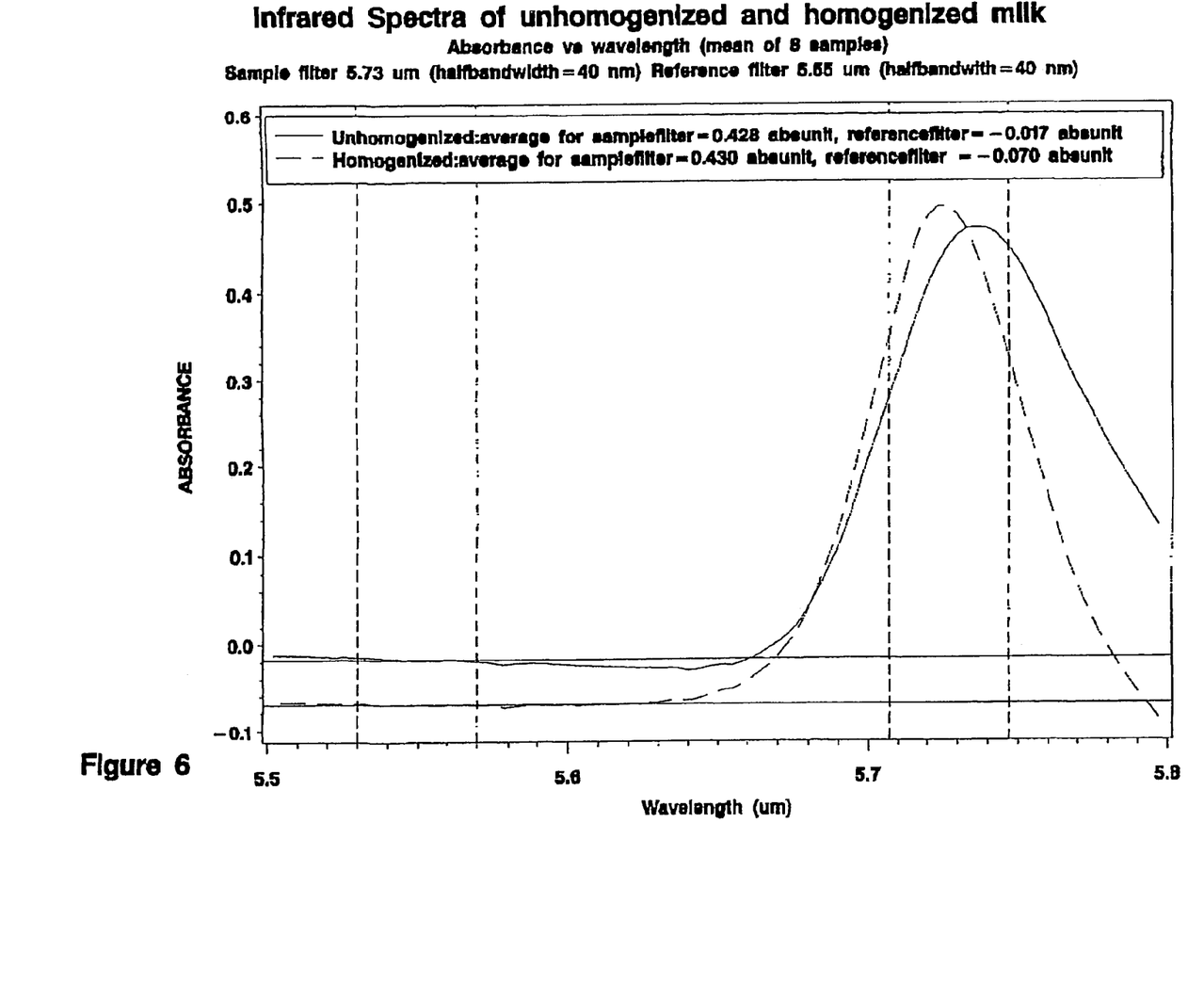
FIG. 6 shows average absorbance spectrum of homogenized and unhomogenized milk samples. The vertical lines are wavebands for reference (center 5.55 μm) and sample (center 5.73) wavebands.
Figure 8:
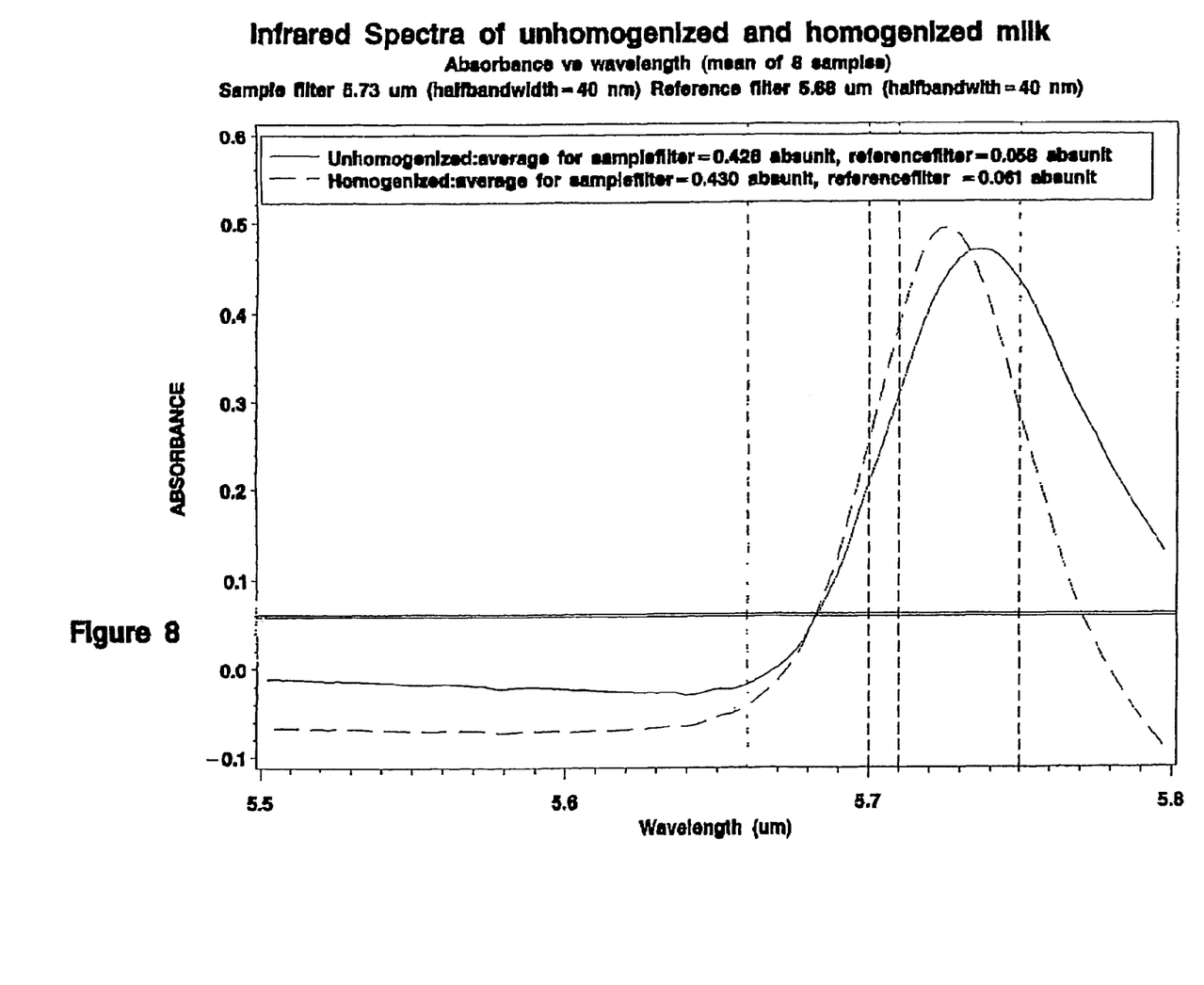
FIG. 8 shows average absorbance spectrum of homogenized and unhomogenized milk samples. The vertical lines are wavebands for reference (center 5.68 μm) and sample (center 5.73) wavebands.

Eight raw milk samples from individual cows were obtained, and each sample was divided into 2 subsamples. One set of subsamples was homogenized for 5 sec. by a homogenizer, LOSmixer, manufactured by L O Sjaunja AB. The raw milk (unhomogenized) and the homogenized milk samples were determined with a FTIR spectrometer, Perkin-Elmer 1720. All samples were warmed up to about 35° C. and carefully mixed, so the creamed fat was evenly distributed in the milk sample, before determination. The liquid cell had a spacer of about 36 μm and the cell windows were calciumfluoride (CaF$_2$). All transmission/absorbance data were against distilled water. The average absorbance was calculated for different bandwidths, as shown in FIGS. 6–8.

In this example, four different combinations are presented. In trial A (FIG. 6) the sample waveband is chosen with a center peak of 5.727 μm and with a bandwidth of 0.040 μm and the reference waveband with a center peak of 5.550 μm with a center band width of 0.040 μm. Band widths can be selected over a relatively large range, e.g. 0.010–0.200 μm, 0.030–0.150, most preferably about 0.100 μm.

| Trial | Treatment | Sample waveband (s) Abs. Unit | Reference waveband (r) Abs. Unit | Difference (s − r) Abs. Unit | Relative |
|---|---|---|---|---|---|
| A | Hom | 0.430 | −0.070 | 0.500 | 1.124 |
|   | Unhom | 0.428 | −0.017 | 0.445 |   |
| B | Hom | 0.381 | −0.070 | 0.451 | 0.989 |
|   | Unhom | 0.439 | −0.017 | 0.456 |   |
| C | Hom | 0.430 | 0.061 | 0.370 | 1.000 |
|   | Unhom | 0.428 | 0.058 | 0.370 |   |
| D | Hom | 0.273 | −0.069 | 0.342 | 1.006 |
|   | Unhom | 0.323 | −0.017 | 0.340 |   |

The relative values are the ratio of the absorbance between homogenized and unhomogenized determinations. It is known that the negative absorbance values determined at the reference wavebands are solely due to water displacement effect. In this example only three examples, B–D, are given, how it is possible to compensate for variations in fat globule size in wavebands regions where the so called Christiansen effect is influencing the waveband shape of fat.

It is also possible to combine three wavebands, two sample wavebands (one about 3.5 µm and one about 5.7 µm) relative to a reference waveband. For example, the determination at about 3.5 µm results in an underestimation for the unhomogenized milk compared to homogenized milk. The reverse situation is at hand in the 5.7 µm region, and thus these two wavebands are inversely influenced by the variation in mean particle size. By taking the average between the two sample wavebands a compensation for variations in mean fat globule size will result. This method of combining at least two wavebands for the purpose of compensating for waveband shifts in regions where the Christiansen effect is causing major analytical problem, is not known to have been disclosed previously.

EXAMPLE 2

The combination of two wavebands was tested in a prototype, which comprises a pulsable IR emitter, thermostated cuvette and an integrated filter and detector unit. The unit is a very compact apparatus and the distance between emitter and detector is only 10 mm (the distance can in principle be smaller, e.g. 5 mm). The filter detector unit comprises in total four infrared interference filter. The filters were a reference, fat, protein (6.50 µm) and lactose (9.60 µm) filter, which are well known and used in commercial apparatus. In this trial, two different filter/detector units were used. The two units only differ in the waveband specification for the fat interference filter. The specification of the waveband filters of reference and fat were as given in FIG. 6 and 7.

Figure 9:
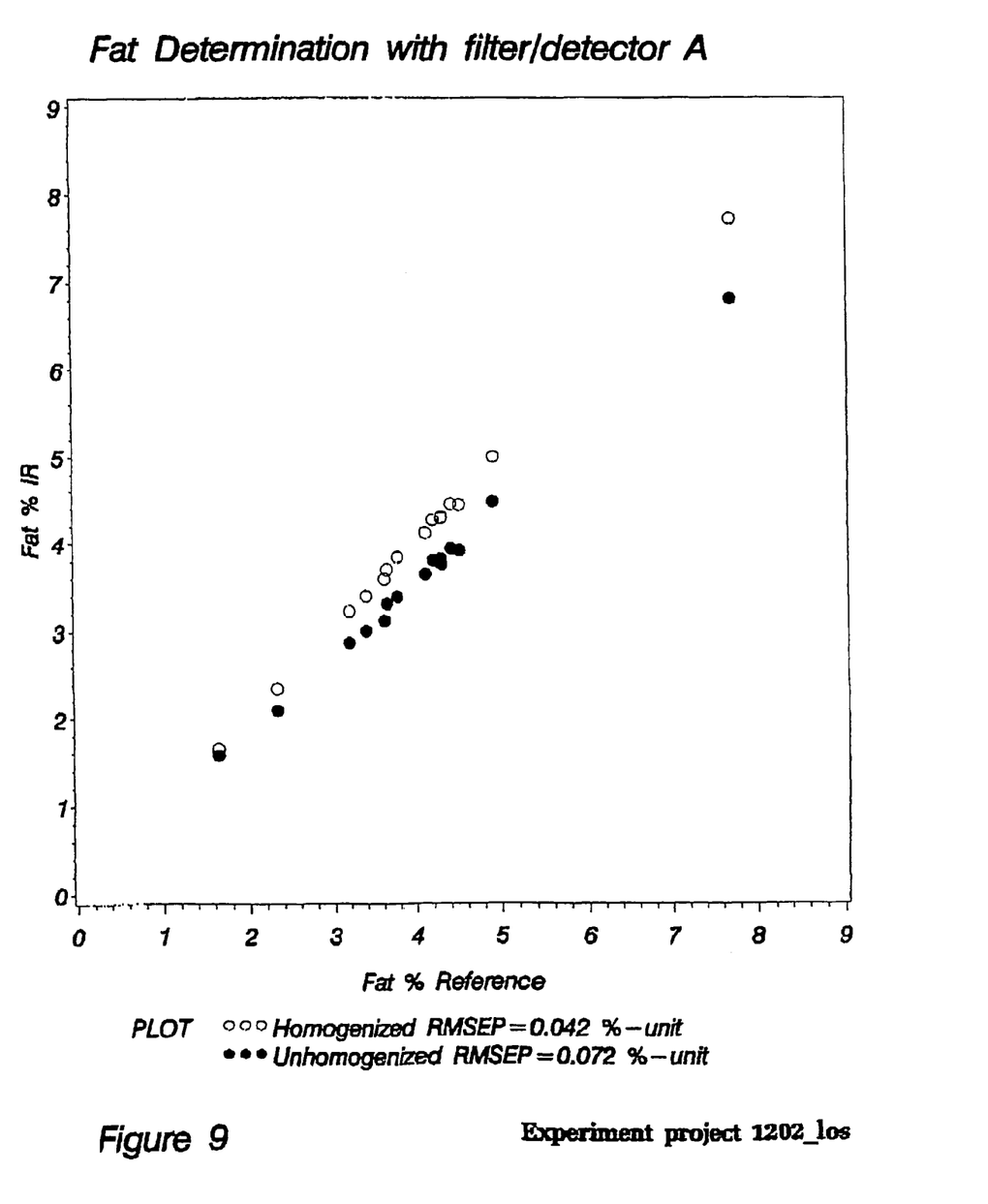
FIG. 9 shows the results achieved by infrared filter/detector unit A of unhomogenized and homogenized milk samples.
Figure 10:
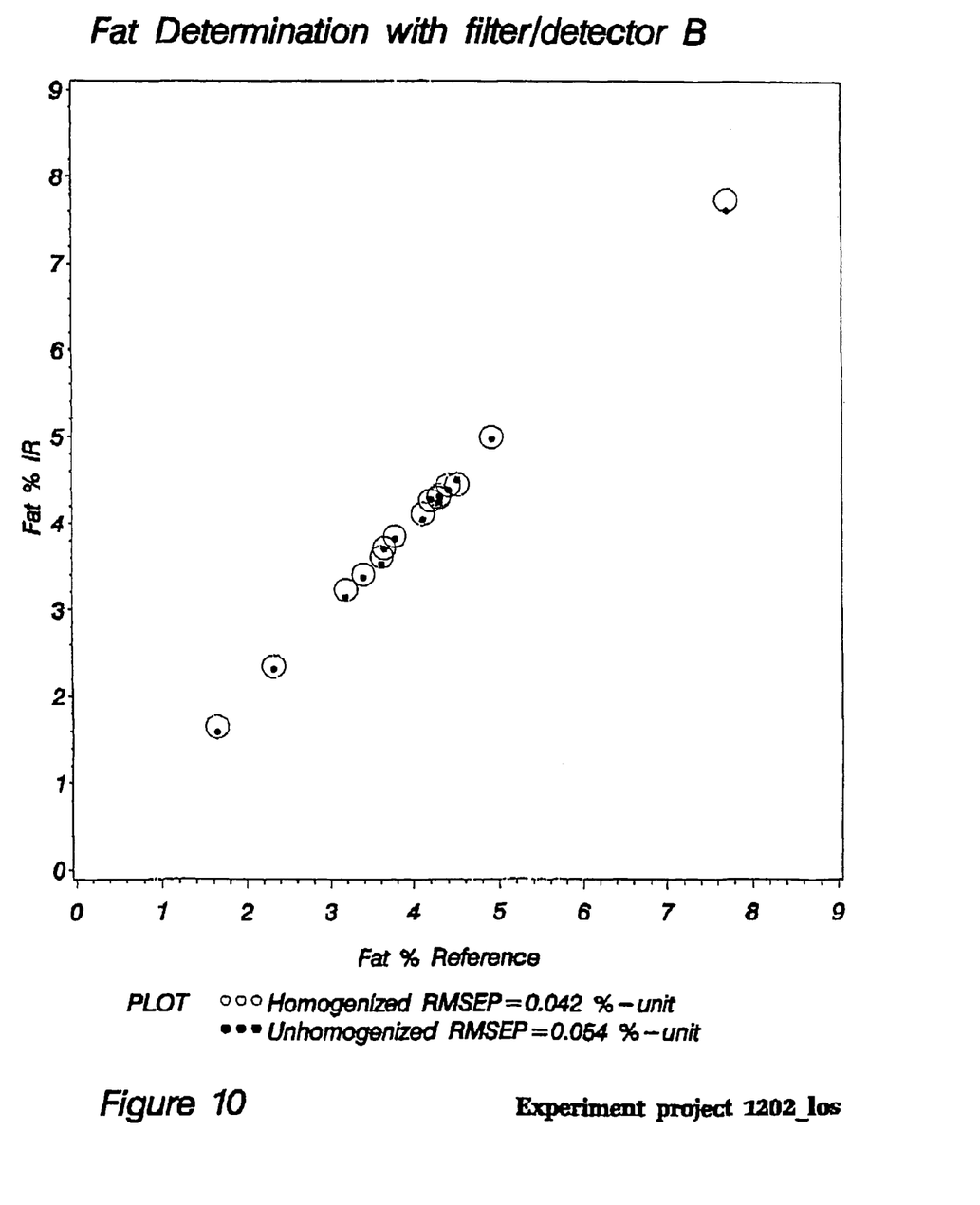
FIG. 10 shows the results achieved by infrared filter/detector unit B of unhomogenized and homogenized milk samples.

Fifteen individual raw cow milk samples, with known composition (reference chemical results), were used in this study. One series of the fifteen samples were homogenized for 5 sec. with a homogenizer, LOSmixer, manufactured by L O SJAUNJA AB, Sweden. In the first embodiment, the filter/detector unit had a fat waveband specification as given in FIG. 6. Before the determination was performed all samples were warmed to about 35° C. in a waterbath and gently mixed by turning the samples up and down, so the creamed fat was evenly distributed in the milk. The milk was then injected by a hand-syringe into the cuvette and the absorbance values for each waveband was determined for both the unhomogenized and homogenized milks. The same procedure was repeated with the second filter/detector unit according to FIG. 7. The absorbance values of distilled water was subtracted from the absorbance values of each milk samples and waveband. The absorbance values of fat, protein and lactose was subtracted from the absorbance values of the reference waveband, as described in formula (2) earlier. The calibration according to formula (5) was performed on the homogenized milk samples for each of the two filter/detector units. In FIG. 9 are the results of fat determination presented of the trial A of homogenized and unhomogenized milk. The determination of unhomogenized milks was on average underestimated by 0.43 percentage units. The determination by the inventive filter combination gave almost equal average results for homogenized and unhomogenized milk samples (FIG. 10). There was only 0.025 percentage units underestimation for the unhomogenized milks. As expected a larger linearity factor was estimated for the waveband where the center was aside of the fat waveband. More surprisingly was that the accuracy was only 0.012(2) RMSEP (Root Mean square of prediction) units higher for the unhomogenized milk. It implies that effect of light scattering is a function of the mean globule size and probable not of the fat globule distribution. The irradiated volume in the cuvette was very low, about 0.003–0.004 cm$^3$. A raw milk with 3.5% fat has about $10^{10}$ fat globules per cm$^3$, so even with this short pathlength it will be found about 30–40 millions fat globules per irradiated volume. It implies that there is a very large number of fat globules per subsample, decreasing the need for repeated measurements per sample. The findings in this investigation has shown that by carefully selecting the exact waveband combination, a nearly independent determination can be achieved for variations in the degree of homogenization.

In a further aspect of the invention there is provided a filter combination that provides a first window at a wavelength, off-peak with respect to the transmission minimum for a homogenized sample, and a second window at a reference wavelength such that the above discussed condition is met.

Suitably interference filters can be used, but any kind of filters that fulfills the purpose and gives the inventive effect is of course equally usable, and are included within the scope of the claims defining the invention.

The filter device can be provided as a separate filter unit that is replaceable if required. However, in the system according to the invention, to be described below, it can be integrated in the detector unit.

By employing FT (Fourier Transform) it is possible to implement the inventive filter in software. Thus, suitably data processing with a computer coupled to the analysis equipment, will enable the operation of the inventive method without having to physically provide a filter device in the light path of the analysis light source.

Now an embodiment of an apparatus for on-site analysis according to the invention will be described with reference to FIGS. 11a and 11b.

Figure 11:
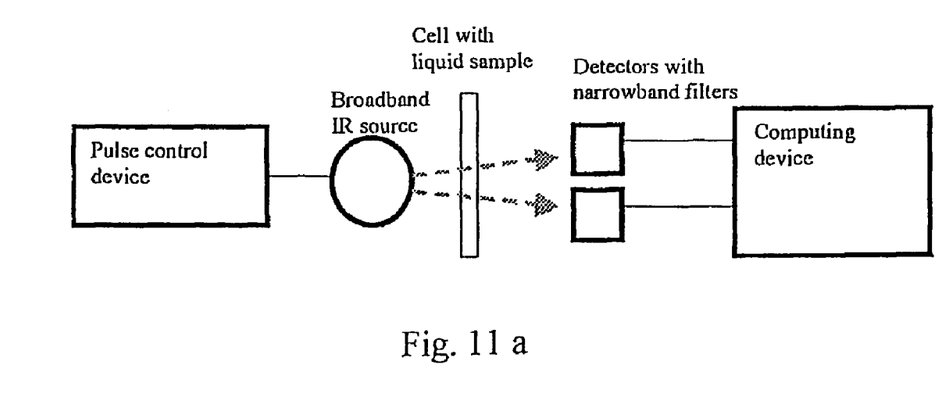

FIGS. 11a and 11b are schematic illustrations of embodiments of a system implementing the inventive idea. Generally it comprises a radiation source that can be of a broadband type (FIG. 11a) or a plurality (e.g. two) narrowband radiation sources (FIG. 11b). In the light path a sample cell is placed and in the first embodiment (FIG. 11a) there are two or more detectors having narrowband filters, for measurement wavebands and reference wave band respectively.

The other embodiment on the other hand comprises a single broad band detector and narrow band radiation sources.

The analysis result will be the same for both embodiments.

Furthermore, as already indicated, by employing Fourier Transform computation, the physical filters can be dispensed with, and the inventive filter selection can be made computationally in the processing unit by suitable software.

The inventive filter device described above, is preferably attached in front of the detector board between the board and the detector piece of the cuvette unit. Thereby of course the reference and measurement windows should be aligned with the reference and measurement detectors, respectively.

The invention having been described with reference to specific embodiments, is subject to alterations and modifications pertaining to the field of the skilled man, and the scope of invention is to be construed on the basis of the appended claims.

The invention claimed is:

1. A method of quantitative measurement of fat in a liquid sample by an infrared attenuation technique, wherein the fat is present in the form of an emulsion of particles causing Christiansen's effect, i.e. the combined effect of lightscattering and anomalous dispersion, the method comprising transmitting infrared radiation through the sample, determining the infrared absorption of the sample in at least one measurement waveband exhibiting Christiansen's effect, located in the region of 5.7 µm, or at 3.5 µm or both, with a bandwidth of about 0.010–0.200 µm and with reference to a reference waveband, such that the sample waveband has an effective waveband, which is off-set or displaced from the absorbance peak for homogenized milk, where unhomogenized milks have higher absorbance than homogenized milks and selecting the reference waveband where unhomogenized milks have higher absorbance than homogenized milks, whereby the fat determination is essentially independent of Christiansen's effect.

2. The method as claimed in claim 1, wherein said reference waveband is located at 5.55 µm, with a band width of about 0.010–0.200 µm.

3. The method as claimed in claim 1, wherein an average of measurement wavebands is calculated, said measurement wavebands being inversely influenced by the variation of said mean particle size.

4. The method as claimed in claim 1, wherein the liquid sample is unhomogenized milk.

5. The method of claim 1 wherein, the bandwidth is 0.030–0.150 µm.

6. The method of claim 1 wherein, the bandwidth is about 0.100 µm.

7. The method of claim 1, wherein said reference waveband is located at 5.55 µm, with a band width of 0.030–0.150 µm.

8. The method of claim 1, wherein said reference waveband is located at 5.55 µm, with a band width of about 0.100 µm.

* * * * *